US012622692B2

(12) United States Patent
Flöss et al.

(10) Patent No.: US 12,622,692 B2
(45) Date of Patent: May 12, 2026

(54) TENDON FIXATION PLATE

(71) Applicant: INOVEDIS GmbH, Albstadt (DE)

(72) Inventors: Lukas Flöss, Inneringen (DE); Stefan Welte, Albstadt (DE)

(73) Assignee: INOVEDIS GMBH, Albstadt (DE)

( * ) Notice: Subject to any disclaimer, the term of this patent is extended or adjusted under 35 U.S.C. 154(b) by 13 days.

(21) Appl. No.: 18/733,236

(22) Filed: Jun. 4, 2024

(65) Prior Publication Data

US 2024/0341755 A1     Oct. 17, 2024

Related U.S. Application Data

(63) Continuation-in-part of application No. 17/998,707, filed as application No. PCT/EP2021/062411 on May 11, 2021, now abandoned.

(30) Foreign Application Priority Data

May 14, 2020    (DE) .......................... 102020113146.1

(51) Int. Cl.
    *A61B 17/064*        (2006.01)
    *A61B 17/80*         (2006.01)
          (Continued)

(52) U.S. Cl.
    CPC ...... *A61B 17/0642* (2013.01); *A61B 17/0644* (2013.01); *A61B 2017/0647* (2013.01);
          (Continued)

(58) Field of Classification Search
    CPC ............ A61B 17/0642; A61B 17/8028; A61B 17/8605; A61B 17/861; A61B 17/8615;
          (Continued)

(56) References Cited

U.S. PATENT DOCUMENTS 4,793,335 A  *  12/1988  Frey .................. A61B 17/0642
                                                606/291
4,960,420 A      10/1990  Goble et al.
          (Continued)

FOREIGN PATENT DOCUMENTS

CA          2409331 A1     11/2001
CN       101014293 A        8/2007
          (Continued)

OTHER PUBLICATIONS

First Office Action for New Zealand Patent Application 795590, dated Jun. 13, 2024, 5 pages.
          (Continued)

*Primary Examiner* — Marcela I. Shirsat
(74) *Attorney, Agent, or Firm* — Christopher J. Volkmann; KELLY, HOLT & CHRISTENSON PLLC

(57)              ABSTRACT

A tendon implant for planar connection of tissue to bone includes a clamping surface that includes an outer edge, an inner edge, and at least one connecting web. At least one of the outer edge is connected at least partially to the inner edge at least partially by the at least one connecting web or the clamping surface includes at least one opening arranged within the clamping surface. The at least one opening is connected by the at least one connecting web. The clamping surface has a circular or oval or polygonal circumference, and includes a rotationally symmetrical and/or mirror-symmetrical contour. The clamping surface has a further opening configured to receive a securing means. The securing means includes a pin, a head and a neck. The clamping surface includes at least one projection, and the at least one projection includes an articulated joint.

23 Claims, 3 Drawing Sheets

(51) Int. Cl.
   *A61B 17/86*       (2006.01)
   *A61F 2/08*        (2006.01)

(52) U.S. Cl.
   CPC ... *A61B 2017/0648* (2013.01); *A61B 17/8047*
        (2013.01); *A61B 17/809* (2013.01); *A61B*
        *17/8605* (2013.01); *A61B 17/861* (2013.01);
        *A61B 2017/8655* (2013.01); *A61B 17/8665*
        (2013.01); *A61B 17/8695* (2013.01); *A61F*
        *2/0811* (2013.01); *A61F 2002/0817* (2013.01);
        *A61F 2002/0847* (2013.01); *A61F 2002/0858*
        (2013.01); *A61F 2002/0864* (2013.01); *A61F*
        *2002/0888* (2013.01); *A61F 2220/0016*
        (2013.01); *A61F 2220/0041* (2013.01)

(58) Field of Classification Search
   CPC ............ A61B 17/8665; A61B 17/8695; A61B
        17/8047; A61B 2017/0648; A61B
        2017/0647; A61B 2017/8655; A61F
        2/0811; A61F 2002/0858; A61F
        2002/0864; A61F 2002/0829; A61F
        2002/0888; A61F 2002/0817; A61F
        2002/0847; A61F 2220/0016; A61F
        2220/0041
   USPC ......................................................... 606/300
   See application file for complete search history.

(56) References Cited

U.S. PATENT DOCUMENTS

| | | | |
|---|---|---|---|
| 4,988,351 A * | 1/1991 | Paulos .................. | A61F 2/0811 |
| | | | 623/13.12 |
| 5,741,282 A * | 4/1998 | Anspach, III ...... | A61B 17/0401 |
| | | | 606/68 |
| 5,931,869 A * | 8/1999 | Boucher ............ | A61B 17/1714 |
| | | | 606/301 |
| 6,117,139 A | 9/2000 | Shino | |
| 6,248,108 B1 | 6/2001 | Tormala et al. | |
| 2007/0118128 A1 | 5/2007 | Light et al. | |
| 2013/0096678 A1 | 4/2013 | Denham | |
| 2014/0005729 A1 * | 1/2014 | DiMatteo ........... | A61B 17/0401 |
| | | | 606/232 |
| 2016/0100932 A1 | 4/2016 | Kumar | |
| 2016/0100933 A1 | 4/2016 | Linder et al. | |
| 2016/0242771 A1 | 8/2016 | Weinstein et al. | |
| 2017/0100176 A1 | 4/2017 | Kumar | |
| 2017/0181840 A1 | 6/2017 | Floess et al. | |
| 2018/0168798 A1 | 6/2018 | Ricci et al. | |

FOREIGN PATENT DOCUMENTS

| | | | |
|---|---|---|---|
| CN | 110167471 A | 8/2019 | |
| DE | 69705489 T2 | 5/2002 | |
| DE | 102016124593 A1 | 6/2017 | |
| EP | 0358372 A1 | 3/1990 | |
| EP | 3184078 81 | 10/2020 | |
| JP | H02088049 A | 3/1990 | |
| JP | 2006507098 A | 3/2006 | |
| JP | 2000237217 A | 9/2009 | |
| KR | 20040091652 A | 10/2004 | |
| KR | 20140128896 A | 11/2014 | |
| KR | 20180048325 A | 5/2018 | |
| KR | 20200049787 A | 5/2020 | |
| WO | 2019157853 A1 | 8/2019 | |

OTHER PUBLICATIONS

Russian Patent Application No. 2022132571/14 Russian Office Action dated May 11, 2021, 18 pages, which correlates to U.S. Appl. No. 17/998,707.

First Japanese Office Action for Japanese Patent Application No. 2022-569591, dated Jun. 27, 2023, 5 pages.

International Search Report and Written Opinion for International Patent Application No. PCT/EP2021/062411, dated Aug. 9, 2021, 15 pages with English Translation of Search Report.

Office Action for German Patent Application No. 102020113146.1, dated Dec. 16, 2020, 9 pages.

International Preliminary Report on Patentability for International Patent Application No. PCT/EP2021/062411 dated Aug. 30, 2022, 47 pages.

English Translation of the International Preliminary Report on Patentability for International Patent Application No. PCT/EP2021/062411 dated Aug. 30, 2022, 7 pages.

Office action for Indian Application No. IN202247071504 mailed Sep. 26, 2025, 5 Pages.

Notice of Reasons for Rejection for Japanese Application No. 2024-095943, dated Jul. 15, 2025, 23 pages.

Office Action for Canadian Application No. 3186602, dated Dec. 1, 2025, 6 Pages.

\* cited by examiner

TENDON FIXATION PLATE

CROSS-REFERENCES TO RELATED APPLICATIONS

This application is a continuation-in-part and claims priority to U.S. application Ser. No. 17/998,707, filed Nov. 14, 2022, which is a Section 371 National Stage Application of International Application No. PCT/EP2021/062411, filed May 11, 2021, and published as WO 2021/228807 A1 on Nov. 18, 2021, and claims priority to German Application No. 102020113146.1, filed May 14, 2020; the contents of each of these applications are hereby incorporated by reference in their entirety.

DETAILED DESCRIPTION

Figure 1:
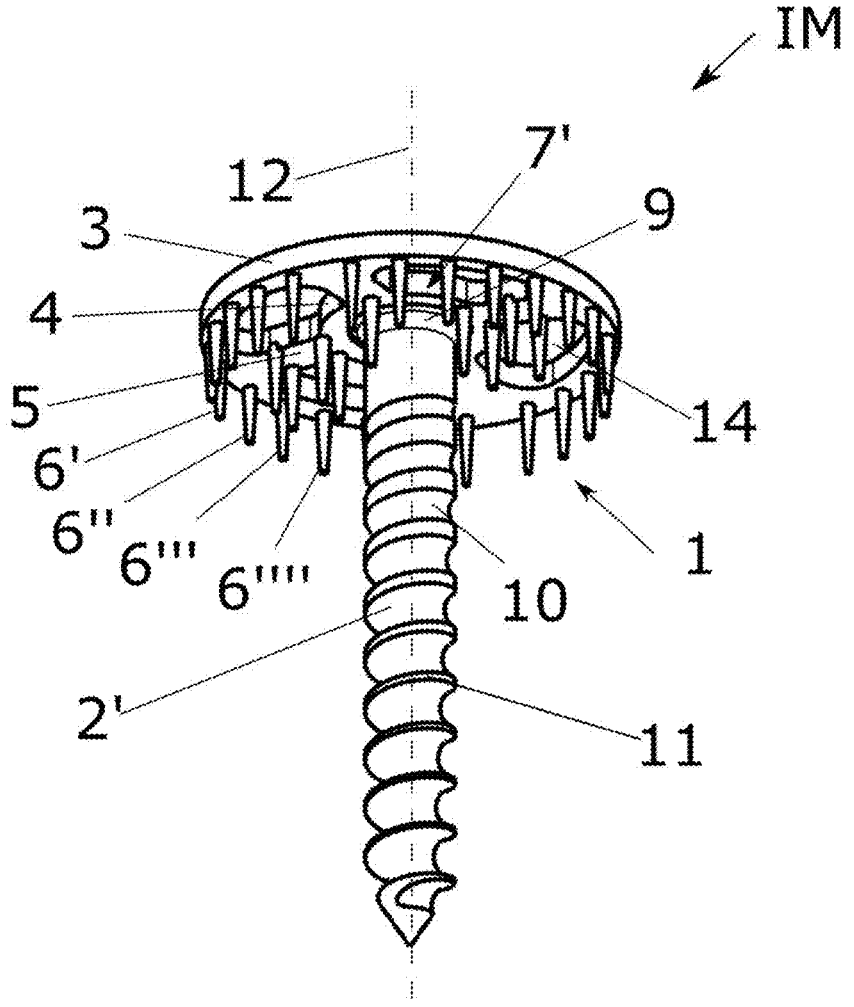
FIG. 1 shows a perspective illustration of an implant in one example with a screw as securing means.

The present disclosure relates to a tendon implant for planar connection of tissue to bone.

A medical intervention for fixing and reconstructing torn-off tissue, for example tendinous tissue, is a customary procedure and can have different causes. In this regard, it is known from the prior art that, in order to reconstruct, for example, a torn-off tendon, the torn-off tendinous tissue is fixed by means of an implant for incorporation on a bone to said bone. It has to be ensured here, among other things, that there is a sufficient flow of blood through the tendinous tissue to prevent necrotic processes.

An implant of this type is known, for example, from EP 3 184 078 B1. The torn-off tendinous tissue is fixed permanently here to the bone by means of a broken-through clamping surface and at least three securing means connected thereto. The implant is held for fixing purposes by means of a special tool and the securing means are driven into the bone, for example by means of an impact tool. The tissue is thereby connected to and pressed onto the bone in planar fashion. A disadvantage of this is in particular that, for secure holding, the implant has to be driven with its securing means into the bone with extremely great precision. Position, angle and orientation, in which the implant is secured, have to be carefully selected, which means that such a surgical intervention takes more time and therefore entails increased costs.

Furthermore, incorrect driving of the implant into the bone may have an effect on the stability of the implant and cause the tissue to be detached from the bone. As a result, another intervention is necessary, which places additional stress on the patient.

Moreover, a minimally invasive introduction of the implant by the surgical procedure is frequently impossible because of the considerable size of the implant.

Furthermore, WO 2019/157853 A1 discloses a fixation clamp for knee joint surgery for fixing the collateral ligament of the knee joint or for preventing injury to the patella tendon at the Tuberculum tibialis.

Furthermore, EP 0 358 372 A1 discloses a channel ligament clamp, comprising a section of a channel which is produced from a material which is suitable for human implantation, having upright, spaced-apart, parallel spikes.

Furthermore, US 2007/118128 A1 discloses various exemplary methods and devices for fixing an implant to native tissue, for example bone.

Furthermore, US 2013/096678 A1 discloses transplant fixing arrangements which comprise a base element, a compression element and a fastening element.

Furthermore, US 2016/242771 A1 discloses a bone fixation device or bone clamp, comprising a crown portion, an engagement portion and an outer edge which is generally defined between the crown portion and the engagement portion.

An object of one example of the invention is therefore to make available a possibility for securing tissue to bone in the context of a surgical intervention which, while minimizing necrotic processes, can be performed stably and more easily with less expenditure in terms of time and costs.

According to one example of the invention, this object is achieved in conjunction with the preamble of patent claim 1 by the characterizing features of patent claim 1. The dependent claims specify advantageous and expedient developments.

To achieve this object, an implant for planar connection of tissue to bone is proposed, wherein the clamping surface comprises an outer edge and an inner edge, wherein the outer edge is connected at least partially to the inner edge at least partially by means of at least one connecting web, and/or in that the clamping surface comprises an outer edge and at least one opening arranged within the clamping surface, wherein the opening is connected by means of at least one connecting web at least to a partial area of the outer edge of the clamping surface.

According to one example, provision is made here that the clamping surface has a circular or oval or polygonal circumference, in particular a rotationally symmetrical and/or mirror-symmetrical contour, wherein the clamping surface has a further opening, wherein the further opening is designed for receiving a securing means, wherein the securing means comprises a pin, a head and a neck, wherein the projection comprises an articulated joint.

This makes it possible to make available a greatest possible supporting surface or clamping surface and symmetry of the implant for the securing thereof without non-uniform conditions occurring in the contact pressure, for example in distinct corner regions. In addition, this shaping of the implant provides possibilities for use in the sphere of minimally invasive surgery since it can be handled by means of minimally invasive tools and introduced through and positioned by corresponding devices.

Furthermore, this has the advantage of preventing a leverage effect on the tendon or tendon tissue. It ensures only an attachment to the tendon and not crushing it, which can prevent a sudden change of the diameter of the blood vessels of the tendon.

The securing means can be optimally adapted in interaction with the clamping surface and the bone. In addition, it is possible for the securing means to be driven into the bone by means of a special tool, for example a screw driver or an impact adapter.

Moreover, the implant is able to exert a continuous contact pressure, which can be maintained over the entire period of incorporation. To this extent, more rapid incorporation can be made possible.

As a result, the required expenditure of time for an operative intervention can be significantly reduced and the healing process shortened. Advantageously, therefore, a duration of treatment after a surgical intervention, and also treatment costs, can be reduced, since follow-up treatments can be made considerably easier. Possible treatments after introduction of the implant or after connection of tissue and bone can thereby be reduced or even be not needed at all.

Furthermore, provision is made that the further opening in the clamping surface is centered.

This makes it possible to optimally align and place the implant at a desired location, which facilitates the intervention associated therewith. The implant can therefore be secured to the bone in different orientations, for example, which means less expenditure of time and greater flexibility for the surgeon since an optimum alignment can thereby be found more rapidly during the intervention.

In addition, provision is made that the further opening has a hollow for receiving the head with a form fit.

This makes it possible to uniformly and more rapidly secure the clamping surface to the bone. The head of the securing means can thereby be connected to the implant with a form fit and a defined hold, and also a defined alignment between securing means and implant can be made possible without further measures being necessary for this purpose.

Furthermore, provision is made that the neck and the head with the opening form a joint, in particular a joint in the manner of a wobble joint.

This makes it possible for the clamping surface to be able to take up different position angles in relation to the securing means. The clamping surface is therefore flexibly connected to the securing means and bearing against the bone is facilitated.

This is undertaken by tilting the clamping surface in relation to the bone, which permits greater flexibility in the introduction of the implant direction and in the fixing of the tissue.

Moreover, unevennesses and anatomical differences in the bone can thereby be compensated and optimum bearing of the clamping surface permitted. As a result, greater flexibility in the selection of a securing point for the implant is provided, and it can be selected in the best possible way.

In addition, it is provided that the joint permits tilting of the clamping surface with respect to an axis, which is defined by the longitudinal axis of the pin, by between 0° and 65°, in particular 0° and 55°, preferably 0° and 45°, particularly preferably between 0° and 20°.

As a result, the tilting of the clamping surface with respect to the longitudinal axis of the pin is restricted and an angular area created in which the clamping surface of the tendon firstly provides an optimum hold and secondly has the required flexibility for introduction and securing.

In addition, provision is made that the further opening in the clamping surface is eccentric.

This provides the possibility for a surgeon to select the position of the clamping surface relative to the securing means and the tendon to be fixed, which can permit an increase in the flexibility when searching for a suitable site for introduction of the implant.

Furthermore, provision is made that the clamping surface comprises at least one projection, wherein the projection is offset with respect to the clamping surface, wherein the projection has at least one opening, wherein the opening in the projection is designed for receiving a securing means, and wherein a further opening in the projection is designed as a cutout.

As a result, a further possibility for securing the implant can be made available. Moreover, the introduction of the implant during a surgical intervention can be simplified. For example, use can be made of a further securing means which is arranged in the opening in the projection and connects tissue and bone to each other. It can also be made possible for the implant to be able to be secured to tissue and additionally to the bone. Furthermore, the cutout can promote a flow of blood and a supply of oxygen to the tendon and thus promote the healing process.

Furthermore, provision is made that the clamping surface comprises at least two opposite spikes, wherein the spikes are formed on the underside of the clamping surface, and/or wherein the spikes preferably comprise barbs.

The spikes can offer an additional securing possibility, for example for securing the implant in advance. In addition, they can be designed in order to prevent the securing means from being driven in too deeply and a resultantly excessive contact pressure of the clamping surface. The spikes thereby permit introduction of the implant in more rapid and secure fashion.

Furthermore, provision is made that the pin comprises a thread.

By this means, a secure and, if required, re-releasable hold of the securing means can be permitted.

In addition, provision is made that the pin is configured in the form of a sleeve, in particular in the manner of a drive-in sleeve, and/or in that the pin comprises barbs.

By this means, the introduction of the securing means into the bone can be permitted by means of a suitable tool, for example a hardened impact tool.

Furthermore, provision is made that the clamping surface comprises a plurality of fixing means, wherein the fixing means are formed on an underside of the clamping surface, in particular perpendicularly to the clamping surface.

The fixing means provide the tendon with an additional hold on the bone. The tendon is held between clamping surface and bone. Owing to the fact that the abovementioned circular or oval or polygonal, in particular rotationally symmetrical, shaping provides more possibilities for orienting the implant, the fixing means have to be able to always engage in the best possible way in the tendon.

The vertical configuration of the fixing means makes it possible to ensure flexibility during use of the implant and stability during fixing of the tendon. The fixing means prevent slipping of the tissue, for example a tendon, and provide a secure and stable hold of the tendon with little contact pressure of the clamping surface. More rapid incorporation can thereby be permitted, with it being possible to avoid necrotic processes.

In addition, provision is made that the fixing means are integrally formed on the clamping surface in the same material, and/or in that the fixing means are cone-shaped, and/or in that the fixing means are surface-tight.

This ensures a stable connection between fixing means and clamping surface, which assists the secure hold of the tendon on the bone. In addition, simple production of the implant is hereby permitted, which improves the outlay on costs for the production and therefore for the surgical intervention.

Provision may be made for at least the clamping surface and the fixing means to be manufactured from a plastic, in particular a biocompatible plastic. Firstly, such materials have sufficient stability in order to connect tissue and bone to each other. Secondly, materials of this type are readily compatible with the human body.

The cone shape permits rapid penetration of the fixing means in the tendon. By this means, the tendon can be held more easily by the implant and the introduction of the implant can be speeded up during the operative intervention. This makes it possible to reduce the expenditure in terms of time and costs.

Owing to the fact that the fixing means are surface-tight, the underside of the clamping surface is uniformly provided with mutually spaced-apart fixing means in order thereby to ensure as good a surface adhesion as possible to the tendon. This ensures an increase in the engagement surface of the implant in relation to the tissue to be fixed, for example a tendon. A high number over the entire underside of the clamping surface increases the fixing action of the implant and permits a reduction in the contact pressure. In addition, slipping of the tissue, for example a tendon, is thereby prevented.

Furthermore, provision is made that the fixing means are formed with a length of more than 2 millimeters, preferably with a length of between 2 and 6 millimeters, and/or in that the length of the fixing means increases towards the outer edge of the clamping surface.

These lengths are particularly advantageous for fixing tissue, for example tendons, in particular tendons in the area of the human shoulder. A certain length of the fixing means, by the latter penetrating the tissue and subsequently being supported on the bone, prevents an excessive contact pressure on the implant and at the same time ensures that tissue is particularly securely and stably fixed on bone.

The longer fixing means at the outer edge of the clamping surface make it possible to compensate for differences in the contact pressure owing to the centering of the securing means. This ensures improved properties in the fixing of the tendon.

It is thereby also possible to take into consideration individual anatomical circumstances and unevennesses of the bone. As a result, the introduction of the implant or the connection of tissue and bone can be simplified and speeded up. Moreover, increased stability of the hold of tissue and bone can be achieved. Furthermore, a more uniform pressing of the tissue over the entire area of the clamping surface can thereby be achieved.

In addition, provision is made that at least two securing means are arranged approximately parallel to one another and/or have different lengths, and/or in that the clamping surface forms a plane, wherein at least one securing means is arranged approximately perpendicular to the plane and/or at least one securing means is arranged approximately parallel to the plane.

By means of the different design and arrangement of the securing means, individual anatomical circumstances can be taken into consideration. This can result in a reduced expenditure of time for an operative intervention. Furthermore, this can result in an improved hold of the implant and an associated secure connection between tissue and bone.

Furthermore, provision is made that the clamping surface comprises a tool engagement surface and/or tool engagement opening, the engagement surface being free from fixing means.

Stable gripping of the implant for securing same to the bone can permit a time-saving and safe surgical intervention. The position and orientation can be precisely selected by the preferably form-fitting engagement, for example by means of a special tool, for example a forceps holder with inner tool feedthrough, in particular from the sector of minimally invasive surgery.

The absence of fixing means on said engagement surface is advantageous since the tool can thereby be formed more simply and the implant held more securely. The introduction of the implant during an operative intervention can thereby be simplified and speeded up.

In addition, provision is made that the at least one projection is arranged approximately along a transverse extent of the clamping surface, and/or in that the at least one projection and the clamping surface are formed in one piece.

This is a further possibility of securing the implant, for example to the bone. This can make it possible for the connection between tissue and bone to withstand increased loads after the introduction of the implant. Treatments after connection of tissue and bone by means of the implant may therefore be unnecessary.

Furthermore, provision is made that the clamping surface has an at least partially rounded circumference and/or is at least partially curved.

It is thus possible to take individual anatomical circumstances into consideration. In this way, it is possible to simplify and speed up the introduction of the implant or the connection of tissue and bone. Moreover, a stable hold of tissue and bone can be achieved. Moreover, more uniform pressing of the tissue on the entire surface area of the clamping surface is thereby achieved. A clamping surface with a curved shape has the advantage of permitting simple modeling of the implant to the bone.

In addition, provision is made that the projection, in particular the articulated joint, comprise a radius.

An advantage of this is that it provides a simple way of forming an articulated joint.

Furthermore, provision is made that the radius is located in the center of the projection, in particular centered between the securing means (2', 2"), in particular the securing means of the clamping surface (2') and the securing means of the projection (2").

An advantage of this is that the forces acting on the implant or the articulated joint can be optimally distributed, which can be beneficial to the healing process.

In addition, provision is made that the tendon implant is non-rigid, especially shows flexible material properties.

This also has an advantage of optimally distributing the forces acting on the tendon, which can be beneficial to the healing process. Furthermore, the implant is allowed to follow the curvature of the region the implant is placed on. By example when a projection part is used for securing means, this projection part can be slightly bent in a radius and follow the curvature of the tendon or tissue or bone structure below.

Furthermore, provision is made that the tendon implant consists of a plastic or a plastic compound.

An advantage of this is that the implant can be manufactured cost-effectively, but more importantly, the force exerted by the implant on the tendon can also be homogenized, which can be conducive to the best possible healing process.

In addition, provision is made that an expansion of the tendon implant is smaller than 1 cm.

This is an advantageous way of ensuring that the implant is suitable for use in minimally invasive operations and is not too large, in contrast to other implants known in the state of the art. By this the possibility is given that the implant can be slightly elastically deformed when inserted e.g. through a tube during surgery.

Within the context of one example of the invention, the fixing means can also be designated as spikes or small teeth.

Furthermore, within the context of one example of the invention, the securing means can also be designated and understood as a screw, nail or bone anchor. Securing means of this kind can be produced cost-effectively and permit a stable connection between bone and implant.

In addition, within the context of one example of the invention, a drive-in sleeve can be understood as meaning a sleeve with a conical tip which simplifies the penetration of the sleeve into a fixed object, for example a bone.

Further details of examples of the invention are described in the drawings with reference to schematically illustrated exemplary embodiments.

FIG. 1 shows a perspective illustration of an implant IM in one example for planar connection of tissue to bone. This comprises a clamping surface 1 by which the tissue, e.g. tendinous tissue, is fixed and held for incorporation on the bone. The clamping surface 1 comprises an outer edge 3 and an inner edge 4, wherein the outer edge 3 is connected to the inner edge 4 by means of connecting webs 5. The clamping surface 1 furthermore comprises openings 14 which are arranged therein and are surrounded by means of the connecting webs 5 and the outer edge 3 of the clamping surface 1. The openings 14 permit a sufficient flow of blood to the tendinous tissue for the healing process. At the same time, necrotic processes can thereby be prevented since the clamping surface 1 rests in a planar manner on the tendon and peaks of the contact pressure are avoided.

The clamping surface 1 forms a plane and, in the exemplary embodiment shown in FIG. 1, is formed with a circular circumference. In particular, the clamping surface 1 can also be formed with an oval, polygonal, rotationally symmetrical and/or mirror-symmetrical contour. Such shapes make it possible for the clamping surface 1 to bear over a large surface area against the tendon and for contact pressure to be uniformly distributed.

The clamping surface 1 has a centered opening 7'. The latter is designed for receiving a securing means 2'. The implant IM can be stably and securely secured to the bone by means of the securing means 2'.

In this exemplary embodiment, the securing means 2' is designed as a screw 11, comprising a pin 10 in the form of a thread, a head 8 (illustrated in FIG. 2) and a neck 9. A screw 11 affords the advantage by means of a rotational movement of being able to determine the penetration depth into the bone. This provides the possibility of optimally adjusting the contact pressure of the clamping surface against the tissue to be fixed, for example a tendon. Firstly, furthermore, too deep a securing of the implant IM, which may lead to excessive contact pressure, can be corrected by reversing it, and, secondly, a retrospective detachment of the implant IM is made possible by means of a screw 11. A screw 11 can furthermore be anchored in a bone by means of a dowel, which can result in an improved hold in the bone.

The neck 9 and the head 8 (illustrated in FIG. 2) together with the centered opening 7' form a joint in the manner of a wobble joint, as a result of which the position of the clamping surface 1 can be tilted with respect to the longitudinal axis of the pin 12 during the securing of the implant IM. This permits optimum bearing and fixing of the tissue, and the implant IM can be flexibly adapted to anatomical circumstances.

Fixing means are also illustrated, by way of example 6', 6", 6''', 6'''', which enable the fixing of tissue, for example tendinous tissue, simplify a connection or fastening of tissue, for example tendinous tissue, to the bone and reinforce the connection of tissue and bone. The fixing means 6', 6", 6''', 6'''' are formed on the underside of the clamping surface 1. As a result, the tissue can be held between the clamping surface 1 and the bone.

The fixing means 6', 6", 6''', 6'''' are formed perpendicular to the clamping surface 1, as a result of which the implant IM can provide the tissue, e.g. a tendon, with a stable and secure hold. The fixing means 1 are cone-shaped, as a result of which they penetrate in a simple manner into the tissue to be fixed and therefore simplified attachment of the implant IM is made possible.

The fixing means 6', 6", 6''', 6'''' are integrally formed on the clamping surface 1 in the same material, and therefore there is a stable connection between fixing means 6', 6", 6''', 6'''' and clamping surface 1, and the implant IM can be produced simply and rapidly.

By the fixing means 6', 6", 6''', 6'''' being surface-tight on the underside of the clamping surface 1, they can form an improved uniform hold for the tissue. The length of the fixing means 6', 6", 6''', 6'''' is designed to be more than 2 millimeters, preferably to be a length of 2 to 6 millimeters, so that the tissue, for example a human shoulder tendon, can be optimally held.

Figure 2:
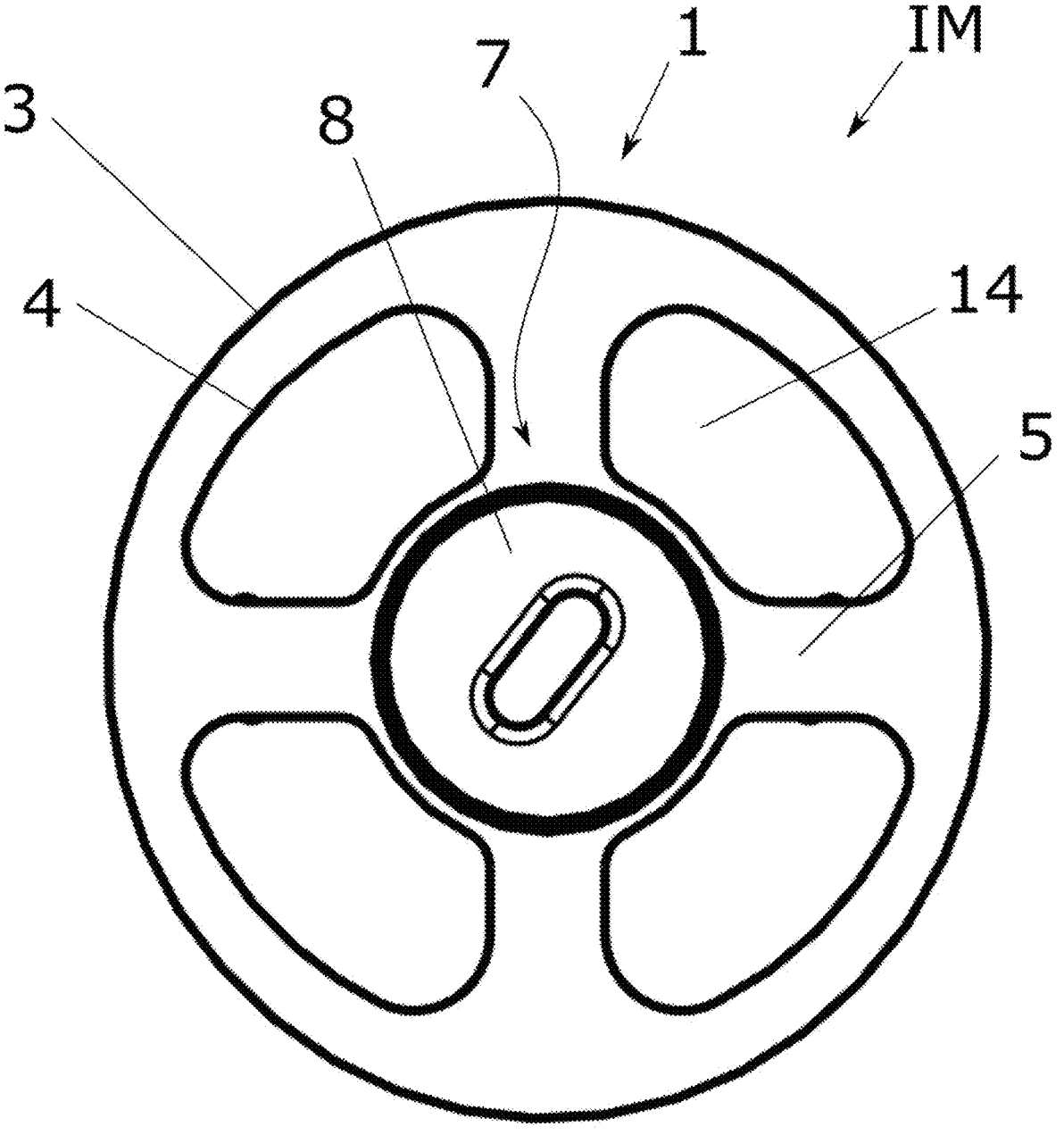
FIG. 2 shows a top view of an implant in one example with a visible head of a screw.

FIG. 2 shows a top view of the embodiment variant which is shown in FIG. 1 of the implant IM with an outer edge 3 and an inner edge 4. The circular circumference of the clamping surface 1 permits the use for minimally invasive surgical interventions. In this top view of FIG. 2, the head 8 of the securing means conceals the opening 7 (not visible) of the implant IM.

The securing means 2', which is designed here as a screw 11, can be screwed into a bone using a suitable special tool. Rapid and simple introduction of the implant is thereby made possible. At the same time, by screwing in the screw 11, the contact pressure of the clamping surface 1 against the tissue to be fixed can be flexibly changed and adjusted. The clamping surface 1 is broken through by the connecting webs 5 and openings 14, also shown in FIG. 1, as a result of which a tissue fixed by it, for example tendonous tissue, has a sufficient flow of blood and necrotic processes are prevented.

A suitable holding tool, or gripping tool, can hold and optimally guide the implant IM during a surgical intervention by way of the connecting webs 5. As a result, the implant can be introduced and secured at a specific site in the bone.

Figure 3:
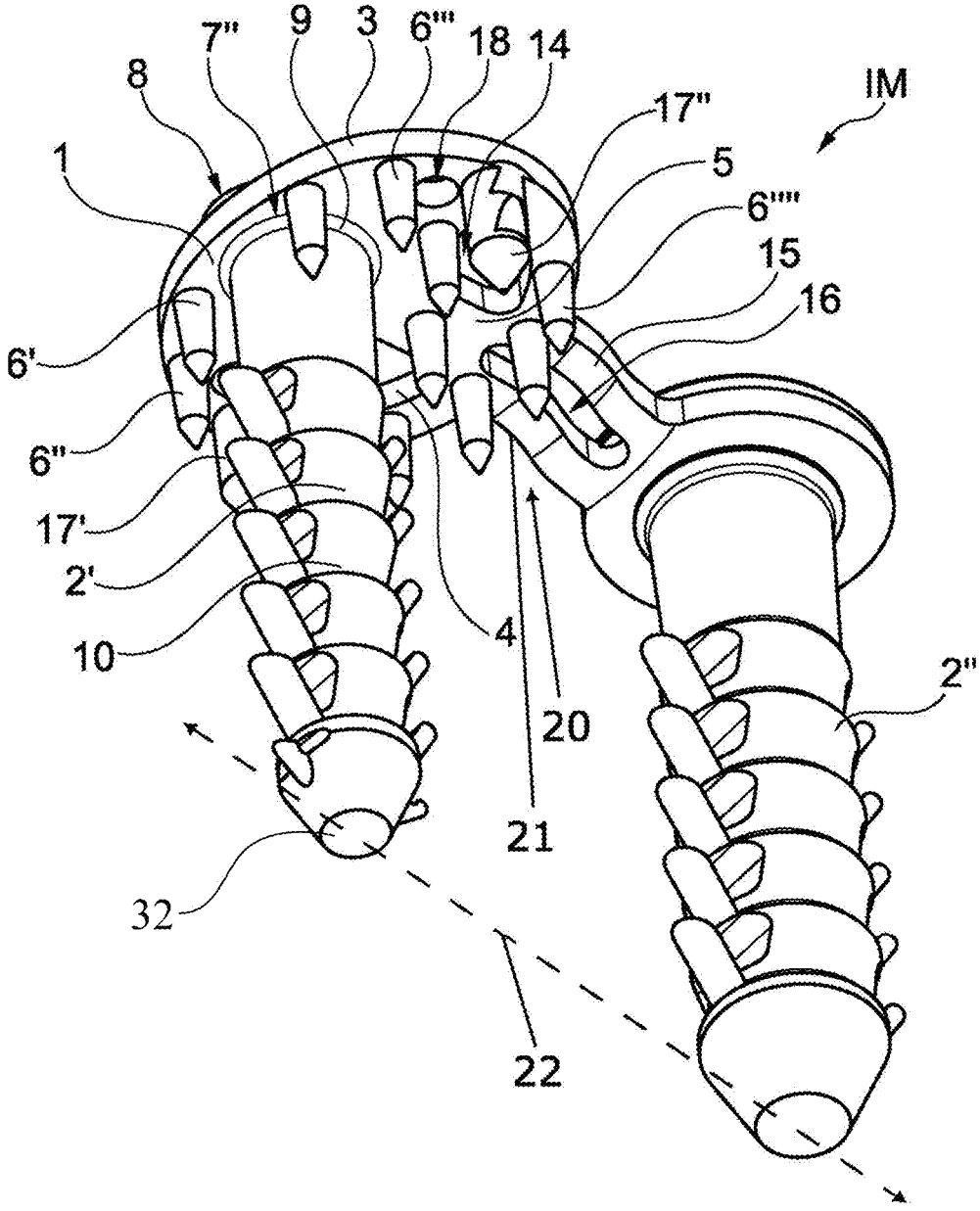
FIG. 3 shows a perspective illustration of an implant according to one embodiment of the invention with projection and two securing means.

FIG. 3 shows an embodiment variant of the implant IM with a projection 15 in a perspective illustration from the underside of the implant. The implant IM for planar connection of tissue to bone comprises the clamping surface 1, the latter comprising the outer edge 3 and the inner edge 4. The outer edge 3 is connected to the inner edge 4 by means of a connecting web 5, and the clamping surface 1 comprises openings 14, 7" arranged within the clamping surface 1, wherein the opening 7" is connected to a partial area of the outer edge 3 by means of a connecting web 5.

The clamping surface 1 has an oval contour and the further opening 7" is formed eccentrically in the clamping surface 1 in order to receive a securing means 2'. By this means, an optimum position of the implant IM relative to tendon and securing means 2' can be selected. The securing means 2' comprises a pin 10, a head 8 (not visible in this illustration), and a neck 9.

The clamping surface 1 comprises a projection 15 which is offset with respect to it, the projection 15 having openings 16, 19, wherein the opening 19 in the projection is designed for receiving a securing means 2", and wherein a further opening 16 in the projection is designed as a cutout. The projection 15 is arranged along a transverse extent of the clamping surface 1 and formed in one piece therewith. In interaction with the eccentrically arranged opening 7" of the clamping surface 1 and of the securing means 2', simple and rapid fixing of the implant IM to the bone is made possible. The further opening 16 in the projection, which opening is designed as a cutout, permits just a small contact surface of the projection 15 against the tissue, which is partially covered by it, and can thereby make a positive contribution to improving the supply of oxygen or flow of blood. Owing to the fact that the projection 15 is offset, too great a contact pressure of the clamping surface 1 against a tendon to be held by it, and resulting necrotic effects, can be prevented. In one example, the projection 15 comprises an articulated joint.

In FIG. 3 it is shown that the length of the fixing means (30) increases towards the outer edge of the clamping surface (1). Furthermore, the neck (9) and the head (8) with the further opening (7', 7") form a joint, in particular a joint in the manner of a wobble joint (31). Furthermore, the pin (10) is configured in the form of a sleeve (32).

It is likewise illustrated in FIG. 3 that the clamping surface comprises the two spikes 17', 17" which are formed on its underside and are opposite each other, the spikes 17', 17" for their part comprising barbs. The pin 10 of the securing means 2', 2" is configured in the form of a sleeve, in the manner of a drive-in sleeve, and likewise comprises barbs. A shaping of this type makes it possible for the securing means 2" to be simply driven into the bone and for said securing means to be secured against inadvertent detachment.

Furthermore, it is illustrated in FIG. 3 that the clamping surface comprises a plurality of fixing means 6', 6", 6'", 6"", wherein the latter are formed integrally on the underside of the clamping surface 1, perpendicularly thereto, in the same material, and are cone-shaped and surface-tight.

Furthermore, it can be seen that the securing means of the clamping surface 1, and the securing means 2" of the projection are arranged parallel to one another and have different lengths, and that the clamping surface 1 forms a plane, wherein the securing means 2' of the clamping surface is arranged perpendicularly to said plane.

Although the present invention has been described with reference to preferred embodiments, workers skilled in the art will recognize that changes may be made in form and detail without departing from the spirit and scope of the invention.

LIST OF REFERENCE SIGNS

IM Implant
1 Clamping surface
2' Securing means (clamping surface)
2" Securing means (projection)
3 Edge (outer)
4 Edge (inner)
5 Connecting web
6' to 6"" Fixing means
7' Opening (central)
7" Opening (eccentric)
8 Head
9 Neck
10 Pin
11 Screw
12 Longitudinal axis of the pin
14 Opening
15 Projection
16 Opening (further, projection)
17', 17" Spike
18 Tool engagement opening

19 Opening (projection)
20 Articulated joint
21 Radius
22 Expansion of the implant
30 Fixing means
31 Wobble joint
32 Sleeve

What is claimed is:

1. A tendon implant for planar connection of tissue to bone, wherein the tendon implant comprises a clamping surface,
   wherein the clamping surface comprises an outer edge, an inner edge, at least one connecting web, and a projection,
   wherein the outer edge is connected at least partially to the inner edge by the at least one connecting web,
   wherein the clamping surface comprises at least one opening formed therein, wherein the at least one opening is connected by the at least one connecting web to a partial area of the outer edge of the clamping surface,
   wherein the clamping surface has a further opening formed therein, wherein the further opening in the clamping surface is configured to receive a first securing means, the securing means comprises a pin, a head and a neck,
   wherein the projection extends from the outer edge of the clamping surface,
   wherein the projection comprises a first aperture formed therein, a second aperture formed therein, and an articulated joint,
   wherein the articulated joint comprises a first portion and a second portion, and
   wherein the first portion is separated from the second portion by the first aperture formed within the projection.

2. The tendon implant as claimed in claim 1, wherein the articulated joint extends from the outer edge of the clamping surface, and wherein the first portion of the articulated joint extends substantially parallel to the second portion of the articulated joint.

3. The tendon implant as claimed in claim 2, wherein the first aperture formed within the projection extends from the outer edge of the clamping surface, and wherein the first aperture extends substantially parallel to the articulated joint.

4. The tendon implant as claimed in claim 1, wherein the second aperture formed within the projection is configured to receive a second securing means, the second securing means comprises a pin, a head, and a neck.

5. The tendon implant as claimed in claim 1, wherein the first portion of the articulated joint comprises a first radius that extends from the clamping surface, and wherein the second portion of the articulated joint comprises a second radius that extends from the clamping surface, the first radius extends substantially parallel to the second radius.

6. The tendon implant as claimed in claim 5, wherein the first radius and the second radius are centered between the first securing means of the clamping surface and a second securing means received by the projection.

7. The tendon implant as claimed in claim 1, wherein the further opening in the clamping surface is centered.

8. The tendon implant as claimed in claim 1, wherein the further opening in the clamping surface has a hollow configured to receive the head with a form fit.

9. The tendon implant as claimed in claim 1, wherein the at least one opening of the clamping surface has a different shape from the further opening of the clamping surface.

10. The tendon implant as claimed in claim 1, wherein the further opening in the clamping surface is eccentric.

11. The tendon implant as claimed in claim 1, wherein the clamping surface comprises at least two opposite spikes, wherein the at least two opposite spikes are formed on an underside of the clamping surface.

12. The tendon implant as claimed in claim 1, wherein the pin comprises a thread or barbs.

13. The tendon implant as claimed in claim 1, wherein the clamping surface comprises a plurality of fixing means, wherein the plurality of fixing means are formed on an underside of the clamping surface perpendicularly to the clamping surface.

14. The tendon implant as claimed in claim 13, wherein
the plurality of fixing means are integrally formed on the clamping surface in the same material,
the plurality of fixing means are formed with a length of more than 2 millimeters,
the plurality of fixing means are cone-shaped, or
the plurality of fixing means are surface-tight.

15. The tendon implant as claimed in claim 13, wherein a length of each fixing means, of the plurality of fixing means, increases towards the outer edge of the clamping surface.

16. The tendon implant as claimed in claim 1,
wherein at least two securing means are arranged approximately parallel to one another,
wherein the clamping surface forms a plane, and
wherein at least one securing means is arranged approximately perpendicular to the plane.

17. The tendon implant as claimed in claim 1, wherein the clamping surface comprises one of:
a tool engagement surface free from fixing means, or
a tool engagement opening.

18. The tendon implant as claimed in claim 1, wherein the clamping surface comprises one of: a circular circumference, an oval circumference, a polygonal circumference, or a partially rounded circumference, and
wherein the clamping surface comprises one of: a rotationally symmetrical contour or a mirror symmetrical contour.

19. The tendon implant as claimed in claim 1, wherein the tendon implant is non-rigid.

20. The tendon implant as claimed in claim 1, wherein the tendon implant consists of a plastic or a plastic compound.

21. The tendon implant as claimed in claim 1, wherein an expansion of the tendon implant is smaller than 1 cm.

22. A tendon implant for planar connection of tissue to bone, wherein the tendon implant comprises:
a clamping surface including:
a first side configured to receive a first securing component, wherein the first securing component extends through the clamping surface;
a second side opposite the first side, the second side including one or more spikes extending perpendicularly from the second side;
an outer edge that defines a circumference of the clamping surface; and
an inner edge connected to the outer edge by at least one connecting web;
a projection extending from the outer edge, wherein the projection includes:
a first aperture formed therein;
a second aperture formed therein, the second aperture configured to receive a second securing component; and
an articulated joint having a first portion and a second portion, wherein the first portion and the second portion are separated by the first aperture formed within the projection.

23. A tendon implant for planar connection of tissue to bone, wherein the tendon implant comprises:
a clamping surface including a plurality of eccentric apertures formed therein, wherein:
a first eccentric aperture, of the plurality of eccentric apertures, is configured to receive a securing component that is configured to engage the tissue;
a second eccentric aperture, of the plurality of eccentric apertures, the second eccentric aperture having a different shape than the first eccentric aperture;
a projection extending from the clamping surface, wherein the projection includes:
a first aperture formed therein;
a second aperture formed therein, the second aperture configured to receive a second securing component; and
an articulated joint having a first portion and a second portion, wherein the first portion and the second portion are separated by the first aperture of the projection.

\* \* \* \* \*